United States Patent
Uchiyama et al.

(10) Patent No.: US 6,880,556 B2
(45) Date of Patent: Apr. 19, 2005

(54) APPARATUS FOR SUPPLYING A THERAPEUTIC OXYGEN GAS

(75) Inventors: Mitsuru Uchiyama, Iwakuni (JP); Katsuhiko Okada, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/884,138

(22) Filed: Jun. 20, 2001

(65) Prior Publication Data

US 2002/0195106 A1 Dec. 26, 2002

(51) Int. Cl.$^7$ ................................................ A62B 9/02
(52) U.S. Cl. ........................... 128/205.24; 128/204.18; 128/204.21; 128/204.23; 128/204.24; 128/204.26
(58) Field of Search ....................... 128/204.18, 204.21, 128/204.23, 204.24, 204.26

(56) References Cited

U.S. PATENT DOCUMENTS

| | | | | | |
|---|---|---|---|---|---|
| 4,520,812 A | * | 6/1985 | Freitag et al. | ......... | 128/204.25 |
| 4,766,894 A | * | 8/1988 | Legrand et al. | ........ | 128/204.21 |
| 4,938,212 A | | 7/1990 | Snook et al. | | |
| 5,148,802 A | * | 9/1992 | Sanders et al. | ........ | 128/204.18 |
| 5,239,995 A | * | 8/1993 | Estes et al. | ............ | 128/204.23 |
| 5,313,937 A | * | 5/1994 | Zdrojkowski | .......... | 128/202.22 |
| RE35,295 E | * | 7/1996 | Estes et al. | ............ | 128/204.23 |
| 5,551,418 A | * | 9/1996 | Estes et al. | ............ | 128/204.23 |
| 5,603,315 A | * | 2/1997 | Sasso, Jr. | ................ | 128/204.18 |
| 5,666,945 A | * | 9/1997 | Davenport | ............. | 128/200.14 |
| 5,701,883 A | * | 12/1997 | Hete et al. | ............. | 128/204.26 |
| 5,735,268 A | * | 4/1998 | Chua et al. | ............. | 128/204.23 |
| 5,794,615 A | * | 8/1998 | Estes | .................... | 128/204.23 |
| 5,803,065 A | * | 9/1998 | Zdrojkowski et al. | . | 128/204.23 |
| 5,865,174 A | * | 2/1999 | Kloeppel | ............... | 128/204.23 |
| 5,937,853 A | * | 8/1999 | Strom | ................... | 128/204.23 |
| 5,970,975 A | * | 10/1999 | Estes et al. | ............ | 128/204.23 |
| 6,029,664 A | * | 2/2000 | Zdrojkowski et al. | . | 128/204.23 |
| 6,067,022 A | * | 5/2000 | Laswick et al. | ............ | 340/626 |
| 6,109,260 A | * | 8/2000 | Bathe | ..................... | 128/203.12 |
| 6,125,846 A | * | 10/2000 | Bathe et al. | ........... | 128/202.22 |
| 6,139,506 A | * | 10/2000 | Heinonen | .................... | 600/532 |
| 6,164,276 A | * | 12/2000 | Bathe et al. | ........... | 128/202.22 |
| 6,269,811 B1 | * | 8/2001 | Duff et al. | ............. | 128/204.21 |
| 6,360,741 B1 | * | 3/2002 | Truschel | ................ | 128/202.22 |
| 6,378,520 B1 | * | 4/2002 | Davenport | ............. | 128/204.26 |
| 6,393,802 B1 | * | 5/2002 | Bowser et al. | ................ | 53/403 |
| 6,401,713 B1 | * | 6/2002 | Hill et al. | .............. | 128/204.21 |
| 6,427,689 B1 | * | 8/2002 | Estes et al. | ............ | 128/204.18 |

(Continued)

FOREIGN PATENT DOCUMENTS

| | | |
|---|---|---|
| JP | 02-031764 A | 2/1990 |
| JP | 08-019615 A | 1/1996 |
| JP | 09-024098 A | 1/1997 |
| JP | 09-285543 A | 11/1997 |
| JP | 2001-129086 A | 5/2001 |

*Primary Examiner*—Henry Bennett
*Assistant Examiner*—Nihir Patel
(74) *Attorney, Agent, or Firm*—Rader, Fishman & Grauer PLLC

(57) ABSTRACT

The apparatus includes a cylinder for containing a pressurized therapeutic oxygen gas, a nasal cannula, adapted to be introduced into a nasal passage of a patient, and a conduit extending between the cylinder and the nasal cannula for directing the therapeutic oxygen gas to the nasal cannula from the cylinder. A pressure sensor is provided on the conduit for detecting the pressure in the conduit. A valve is provided, in the conduit, which allows and blocks the fluid communication between the cylinder and the nasal cannula. A controller controls the operation of the valve in synchronization with the respiration of a patient, based on the changes in the pressure detected by the pressure sensor. The volume of the oxygen therapeutic gas passing through the valve for each respiration is increased, compared with a normal respiration condition, when the respiratory frequency increases.

5 Claims, 3 Drawing Sheets

U.S. PATENT DOCUMENTS

| | | | |
|---|---|---|---|
| 6,439,229 B1 * | 8/2002 | Du et al. | 128/204.23 |
| 6,539,940 B1 * | 4/2003 | Zdrojkowski et al. | 128/204.23 |
| 6,581,592 B1 * | 6/2003 | Bathe et al. | 128/202.22 |
| 6,581,599 B1 * | 6/2003 | Stenzler | 128/204.23 |
| 6,622,726 B1 * | 9/2003 | Du | 128/204.26 |
| 6,629,527 B1 * | 10/2003 | Estes et al. | 128/204.18 |
| 6,651,658 B1 * | 11/2003 | Hill et al. | 128/204.23 |
| 6,786,217 B1 * | 9/2004 | Stenzler | 128/204.23 |

* cited by examiner

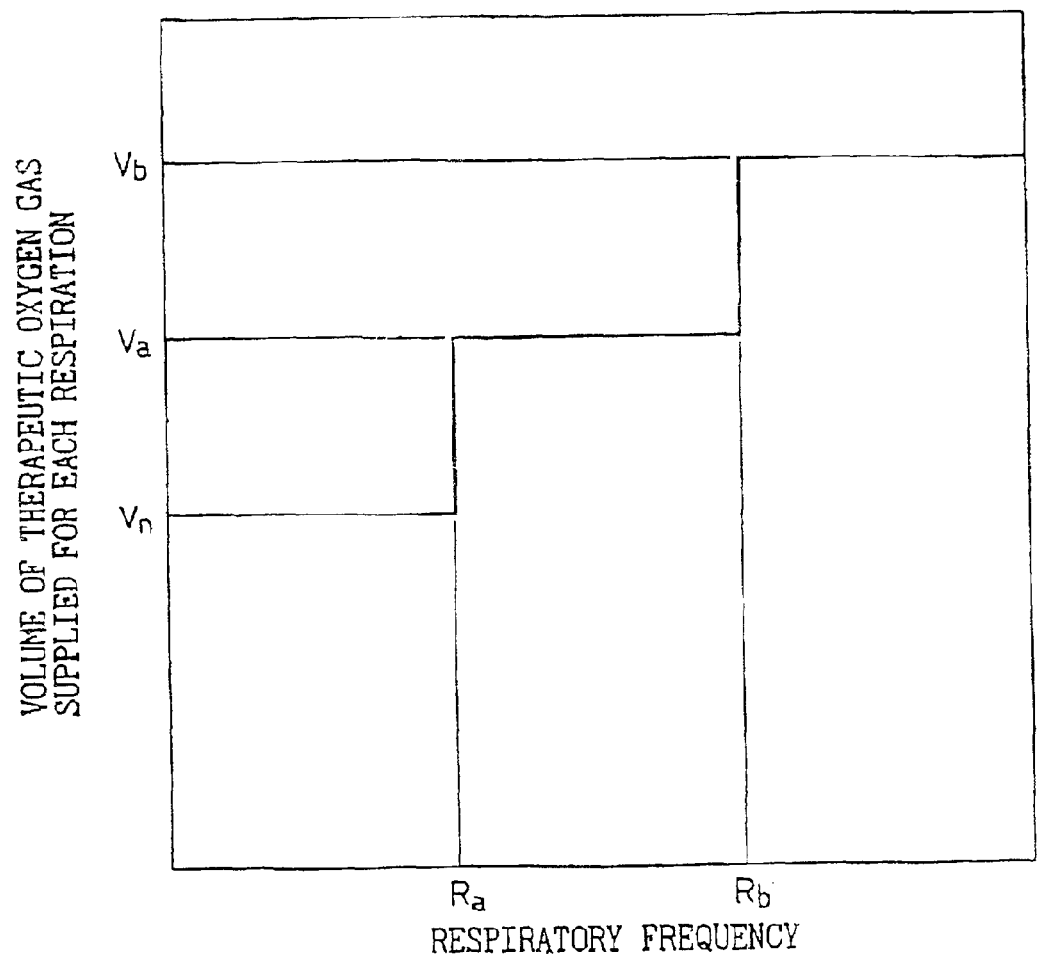

APPARATUS FOR SUPPLYING A THERAPEUTIC OXYGEN GAS

BACKGROUND OF THE INVENTION

1. Field of the Invention

The invention relates to an apparatus for supplying a therapeutic oxygen gas.

2. Description of the Related Art

In treatments for respiratory system diseases such as pulmonary emphysema or chronic bronchitis, oxygen inhalation is known as one of the most effective treatments. In oxygen inhalation therapy, a therapeutic oxygen gas, such as oxygen gas or an oxygen enhanced gas which may be produced by separating nitrogen gas from air, is supplied to the patient with a therapeutic oxygen gas supplying apparatus.

Conventional therapeutic oxygen gas supplying apparatuses supply a therapeutic oxygen gas intermittently, in synchronization with the respiration of a patient, at a constant volume for each respiration. The respiratory frequency, however, is not constant. When the respiratory frequency is increased, in particular when tachypnea is presented, if the therapeutic oxygen gas supplying apparatus supplies the therapeutic oxygen gas at a constant volume for each respiration, dyspnea will result.

SUMMARY OF THE INVENTION

The invention is directed to solve the prior art problems, and to provide an apparatus for supplying a therapeutic oxygen gas improved to change the volume for each respiration in accordance with the respiratory frequency.

According to the invention, there is provided an apparatus for supplying a therapeutic oxygen gas. The apparatus comprises a cylinder for containing pressurized therapeutic oxygen gas, a nasal cannula, adapted to be introduced into a nasal passage of a patient, and a conduit extending between the cylinder and the nasal cannula for directing the therapeutic oxygen gas to the nasal cannula from the cylinder. A pressure sensor is provided on the conduit for detecting the pressure in the conduit. A valve is provided on the conduit, which allows and blocks the fluid communication between the cylinder and the nasal cannula. A controller controls the operation of the valve in synchronization with the respiration of a patient based on the changes in the pressure detected by the pressure sensor. The volume of the therapeutic oxygen gas passing through the valve for each respiration is increased, compared with a normal respiration condition, when the respiratory frequency increases.

DESCRIPTION OF THE DRAWINGS

These and other objects and advantages and further description will now be discussed in connection with the drawings in which:

FIG. 3 is graph which shows the volume of the therapeutic oxygen gas supplied to a patient, the volume increasing in steps according to an increase in respiratory frequency.

DESCRIPTION OF THE PREFERRED EMBODIMENTS

Figure 1:
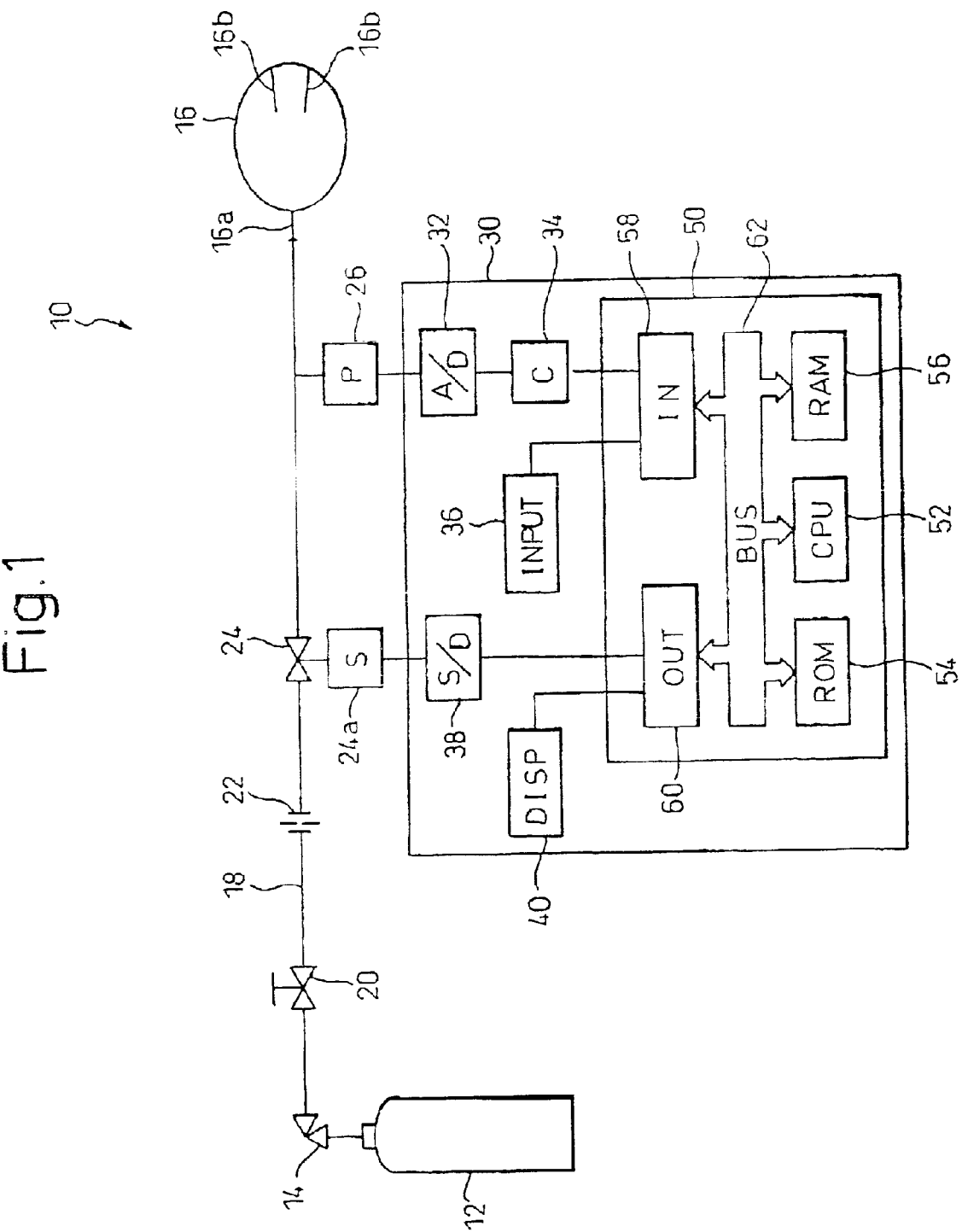
FIG. 1 is a block diagram of a therapeutic oxygen gas supplying apparatus according to an embodiment of the invention.

With reference to FIG. 1, a therapeutic oxygen gas supplying apparatus 10 according an embodiment of the invention supplies a therapeutic oxygen gas, pure oxygen gas or an oxygen enhanced gas, to a patient (not shown) from an oxygen gas cylinder 12 through a conduit 18 and a nasal cannula 16 attached to the face of the patient. The conduit 18 comprises a flexible tube which is, at one of the ends, attached to a shut-off valve 14, connected to the oxygen cylinder 12, and, at the other end, to an inlet port 16a of the nasal cannula 16. The nasal cannula 16 provides means for introducing the therapeutic oxygen gas and includes a pair of cannula portions 16b which are adapted to be introduced into the nasal passages of the patient.

A pressure regulating valve 20 and an orifice 22 are provide on the conduit 18 downstream of the shut-off valve 14. Downstream of the orifice 22, a solenoid operated valve 24 is provided. The pressure regulating valve 20 and an orifice 22 regulate the pressure in the conduit 18 upstream of the solenoid operated valve 24 at a predetermined pressure. The solenoid operated valve 24 includes a solenoid 24a for moving the solenoid operated valve 24 between a first and a second position. At the first position, the solenoid operated valve 24 blocks the flow of the therapeutic oxygen gas, and at the second position, the solenoid operated valve allows the therapeutic oxygen gas to flow therethrough. A pressure sensor 26 is provided on the conduit 18 downstream of the solenoid operated valve 24. The pressure sensor 26 can be any kind of pressure sensor which provides an electric signal representing the pressure in the conduit 18. Preferably, the pressure sensor 26 comprises an electrostatic capacity type pressure sensor having a capacitor of which the capacitance changes in response to the changes in the pressure in the conduit 18.

The apparatus 10 further comprises a controller 30 for controlling the operation of the solenoid operated valve 24 in synchronization with the respiration of the patient. The controller 30 includes an A/D converter 32, a counter 34, a microcomputer 50, an input device 36, a solenoid driver 38 and a display 40. The microcomputer 50 includes CPU (central processing unit) 52, ROM (read-only memory) 54, RAM (random-access memory) 56, an input port 36 and an output ports 60, which are connected to each other through a bidirectional bus 62. The A/D converter 32 is connected to the pressure sensor 32 to receive the electric signal, preferably the capacitance, representing the pressure in the conduit 16. The A/D converter 32 generates electric pulse to the counter 34, connected to the A/D converter 32. The counter 34 is connected to the input port 58 and provides it with a digital signal representing the number of the electric pulse from the A/D converter 32. The input device 36 may comprise keys, buttons or dials for setting parameters for controlling the apparatus 10. The display 40 may comprise liquid crystal display for indicating the parameters, set by the input device 36, and the operational condition of the apparatus 10.

The operational function of the embodiment will be described below.

The pressure sensor 26 presents an electric signal representing the pressure in the conduit 18. For example, if the pressure sensor 26 is an electrostatic capacity type pressure sensor, a capacitance proportional to the pressure in the conduit 18 is transmitted to the A/D converter 32. The A/D converter 32 generates electric pulses of which the number is proportional to the capacitance of the pressure sensor 26. The counter 34 counts the electric pulses from the A/D converter 32 and generates a digital signal corresponding to the number of the electric pulses. The microcomputer 50 determines the initiation of the respiration by monitoring the changes in pressure in the conduit 18 with the digital signal from the counter 34 as follows.

Respiration includes inhalation and expiration. During inhalation, the pressure in the conduit 18 decreases. On the other hand, during expiration, the pressure increases. The ratio between the time periods of inhalation and expiration (I/E ratio) is generally 1/2. The microcomputer 50 differentiates the pressure in the conduit 18 thus obtained. The time when the differentiated pressure is minimum is determined as the initiation of a respiration.

When the microcomputer 50 detects the initiation of a respiration, the microcomputer 50 generates a valve open command to the solenoid driver 38. When the solenoid diver 38 receives the valve open command, the solenoid driver 38 energizes the solenoid 24a to move the solenoid operated valve 24 to the second position whereby the valve 24 opens to allow the oxygen therapeutic gas to flow therethrough. The microcomputer 50 generates the valve open command for a valve opening time long enough to provide the patient with a predetermined volume of the oxygen therapeutic gas prescribed by a doctor, as described below.

Figure 2:
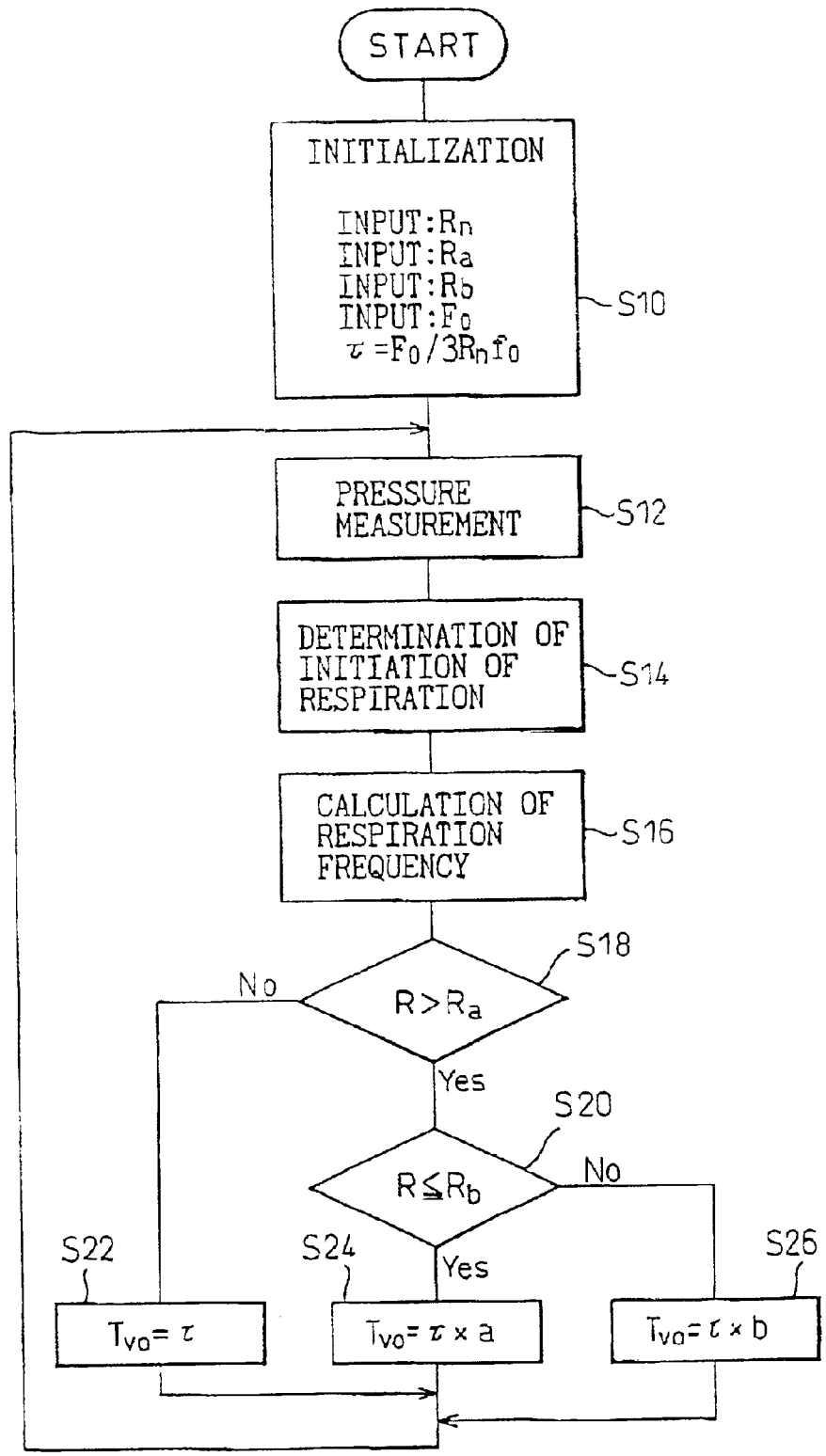
FIG. 2 is a flow chart showing an algorithm of determining the time period for opening the solenoid operated valve.

FIG. 2 is a flow chart showing an algorithm of determining the time period for opening the solenoid operated valve 24. After the activation of the apparatus 10, in step S10, an initialization is carried out wherein the following parameters are input to the microcomputer 50 with the input device 36.

$R_n$: respiratory frequency when the respiration of the patient is normal condition (BPM (breaths par minute))

$R_a$: a first threshold value for respiratory frequency larger than $R_n$(BPM)

$R_b$: a second threshold value for respiratory frequency larger than $R_a$(BPM)

$F_0$: flow rate of oxygen therapeutic gas which may be prescribed by a doctor (m³/min)

In step 10, time period τ (minutes) for opening the solenoid operated valve 24 is calculated by the flowing equation.

$$\tau = F_0 / \alpha R_n f_0 \qquad (1)$$

where:

α: non-dimensional constant $f_c$: flow rate of oxygen therapeutic gas through the solenoid operated valve 24 when the valve 24 is open under the predetermined pressure in the conduit 18 upstream of the valve 24 (m³/min)

The non-dimensional constant α is an inverse of ratio of the time period of inhalation relative to the time period of one respiration, and it can be 3 since the I/E ratio is generally 1/2. If the I/E ratio is not 1/2, the non-dimensional constant α can be altered, accordingly.

The time period τ thus obtained means a time period for opening the solenoid operated valve 24 sufficient for the volume of the oxygen therapeutic gas, which may be prescribed by a doctor, to flow through the valve 24 during inhalation of normal condition.

In steps S12 and S14, the initiation of respiration is determined by monitoring the changes in the pressure, as described above. In step S16, the microcomputer 50 calculates the respiratory frequency R by measuring the time interval between initiations of sequential tow respirations. In step S18, the respiratory frequency R is compared with the first threshold value $R_a$ which is larger than the respiratory frequency $R_n$ under the normal respiration condition. If R is equal to or smaller than $R_a$ ("No" at the step S18), then the respiration is determined as normal, and the time period τ is decided, in step 22, as valve opening time $T_{vo}$ for actually opening the solenoid operated valve 24. If R is larger than $R_a$ ("Yes" at the step S18), then, in step S20, R is further compared with the second threshold value $R_b$. If R is equal to or smaller than $R_b$ ("Yes" at the step S20), then, the respiration is determined as mild tachypnea, and τxa is decided, in step 24, as the valve opening time $T_{vo}$. Here "a" is a predetermined constant larger than 1, and can, for example, be 1.25. If R is larger than $R_b$ ("No" at the step S20) then the respiration is determined as heavy tachypnea, and τxb is decided, in step 26, as the valve opening time $T_{vo}$. Here "b" is a predetermined constant larger than "a", and can, for example, be 1.50.

The microcomputer generates a valve opening command to the solenoid driver 38 for the valve opening time $T_{vo}$. Therefore, the volume of the oxygen therapeutic gas supplied to the patient for each respiration increases in steps according to the increase in the respiratory frequency, as shown in FIG. 3. In FIG. 3, $V_n$ indicates the volume of the therapeutic oxygen gas supplied for each respiration under the normal respiration condition, $V_a$ indicates the volume when the respiratory frequency is above $R_a$, and $V_b$ indicates the volume when the respiratory frequency is above $R_b$.

It will also be understood by those skilled in the art that the forgoing description is a preferred embodiment of the disclosed device and that various changes and modifications may be made without departing from the spirit and scope of the invention.

We claim:

1. An apparatus for supplying an oxygen therapeutic gas, comprising:

a cylinder for containing a pressurized oxygen therapeutic gas;

a nasal cannula, adapted to be introduced into a nasal passage of a patient;

a conduit extending between the cylinder and the nasal cannula for directing the oxygen therapeutic gas to the nasal cannula from the cylinder;

a valve, provided on the conduit, for allowing and blocking the fluid communication between the cylinder and the nasal cannula;

a pressure sensor, provided on the conduit downstream of the valve, for detecting the pressure in the conduit;

an orifice, provided on the conduit upstream of the valve, for regulating pressure in the conduit upstream of the valve; and a controller for controlling the operation of the valve in synchronization with the respiration of a patient based on changes in pressure detected by the pressure sensor, the controller comparing respiratory frequency with a threshold to increase volume of the oxygen therapeutic gas for each respiration in step when the respiratory frequency is larger than the threshold.

2. An apparatus according to claim 1, wherein the valve is a solenoid operated valve having a solenoid, and the controller controls the solenoid to open the valve for a time period sufficient for a volume of the oxygen therapeutic gas to flow therethrough for each respiration.

3. An apparatus according to claim 1, wherein the pressure sensor is an electric capacitor type pressure sensor having a capacitor of which the electrostatic capacitance represents the detected pressure.

4. An apparatus according to claim 1, wherein the controller determines the initiation of each respiration by monitoring the changes in the pressure detected by the pressure sensor.

5. An apparatus according to claim 4, wherein the controller calculates the respiratory frequency by measuring the time interval between the initiations of sequential respirations.

* * * * *